United States Patent
Munro et al.

(10) Patent No.: US 7,135,494 B2
(45) Date of Patent: Nov. 14, 2006

(54) ANTITUMORAL CARBAZOLES

(75) Inventors: Murray Herbert Gibson Munro, Christchurch (NZ); Sylvia Urban, Christchurch (NZ); John Wilson Blunt, Christchurch (NZ); Dolores Garcia Gravalos, Madrid (ES)

(73) Assignee: Pharma Mar, S.A., Madrid ( * ) Notice: Subject to any disclaimer, the term of this patent is extended or adjusted under 35 U.S.C. 154(b) by 285 days.

(21) Appl. No.: 10/450,594

(22) PCT Filed: Dec. 13, 2001

(86) PCT No.: PCT/GB01/05523

§ 371 (c)(1),
(2), (4) Date: Dec. 3, 2003

(87) PCT Pub. No.: WO02/48107

PCT Pub. Date: Jun. 20, 2002

(65) Prior Publication Data

US 2004/0072890 A1    Apr. 15, 2004

(30) Foreign Application Priority Data

Dec. 13, 2000 (GB) ................. 0030417.0

(51) Int. Cl.
*A61K 31/40* (2006.01)
*C07D 487/00* (2006.01)
(52) U.S. Cl. ................... 514/411; 548/428
(58) Field of Classification Search ........... 514/411; 548/428
See application file for complete search history.

(56) References Cited

FOREIGN PATENT DOCUMENTS

| JP | 3-31257 | 2/1991 |
| JP | 08 157475 | 6/1996 |
| WO | WO 92/21660 | 12/1992 |

OTHER PUBLICATIONS

Boogaard, A. et al. Ring D Modifications of Ellipticine, Part 2. Chlorination of Ellipticine via its N-oxide and Syntheses and Selective Acetylation of 5, 6, 11-Trimethyl-5H-Benzo[b]Carbazole. Tetrahedron. 50:16, pp. 4811-4828 (1994).
Dalton L. et al. Synthesis of the Tumour-Inhibitory Alkaloids, Ellipticine, 9-Methoxyellipticine, and Related Pyrido (4,3-b) Carbazoles. Australian Journal of Chemistry. 20:12, pp. 2715-2727 (Dec. 1967).
Faircloth, G. et al. A Simple Screening Procedure for the Quantitative Measurements of Cytotoxicity to Resting Primary Lymphocyte Cultures. Journal of Tissue Culture Methods. 11:4, pp. 201-205 (1988).
Kaneda, M. et al. Carbazomycins G and H, Novel Carbazomycin-Congeners Containing a Quinol Moiety. J. of Antibiotics. XLI:5, pp. 602-608 (May 1988).
Knolker, H. et al. Transition Metal Complexes in Organic Synthesis, Part 38. Tetrahedron Letters. 38, 23, pp. 4051-5054 (1997).
Monks, A. et al. Feasibility of a high flux anticancer drug screen using a diverse panel of cultured human tumor cell lines. J.Natl. Cancer Inst. 83, pp. 757-766 (1991).
Mosmann. T. Rapid Colorimetric Assay for Cellular Growth and Survival: Application to Proliferation and Cytotoxicity Assays. Journal Immunological Methods. 65:1-2, pp. 55-63 (1983).
Skehan, P. et al. New Colorimetric Cytotoxicity Assay for Anticancer-Drug Screening. Journal of the National Cancer Institute. 82:13, pp. 1107-1112 (Jul. 4, 1990).
Sundberg, R. Five-Membered Ring Systems: Pyrroles and Benzo Derivatives. Heterocyclic Chemistry, vol. 4, pp. 81-94 (1992).
Svoboda, G. et al. Alkaloids of Ochrosia maculate Jacq. (Ochrosia borbonica Gmel.). J. of Pharmaceutical Sciences. 57:10, pp. 1720-1725 (Oct. 1968).
Database Chemabs. Somei, M. Preparation of 1-Hydroxyindole Derivatives as Blood Platelet Aggregation Inhibitors. STN Database accession No. 125:195426, XP002192741, RN:161203-02-7.
Database Chemabs, Sundberg, R. Five-membered Ring Systems. Database accession No. 119:180607, XP002194742. RM54989-33-2.
Database Chemabs. Somei, M. Preparation of Indole Derivatives. Database accession No. 114:247138, CP002192743, RN:125812-48-8, RN:125812-49-9.
Database Chemabs. Zherebtsov, I. Chromatographic Determiantion of Carbazole and its Derivatives. Database accession No. 97:49034, XP002192744, RN: 8234-70-6.
International Search Report PCT/GB 01/05523, Mar. 5, 2002.
Russian language version of Zherbtsov, I. P., et al, "Chromatographic Determination of Carbazole and its Derivatives." Publication Source: Deposited Doc. (1980), SPSTL 641khp-D80.

*Primary Examiner*—Kamal A. Saeed
*Assistant Examiner*—Robert Shiao
(74) *Attorney, Agent, or Firm*—Fish & Richardson P.C.

(57) ABSTRACT

The invention provides a compound of formula (I). This invention relates to heterocyclic compounds. It further relates to methods for their preparation, compositions cotaining them and their use as a medicament, particularly as a medicament for the treatment and prophylaxis of cancer.

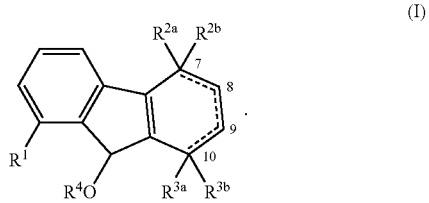

28 Claims, No Drawings

ANTITUMORAL CARBAZOLES

FIELD OF THE INVENTION

This invention relates to heterocyclic compounds. It further relates to methods for their preparation, compositions containing them and their use as a medicament, particularly as a medicament for the treatment and prophylaxis of cancer.

DESCRIPTION OF THE PRIOR ART

The compounds believed to be closest in structure to those of the present invention are carbazomycins G and H [compounds (A) and (B)], which were isolated from the culture broth of *Streptoverticillium ehimense* in 1988: see Kaneda, et al., *J. Antibiot*. 1988, 41, 603. Carbazomycin G was found to have some antimicrobial properties and the total synthesis of carbazomycins G and H has been reported: see Knölker, et al. *Tetrahedron Lett*. 1997, 38, 4051.

Another compound close in structure to the compounds of the present invention is the plant alkaloid ellipticine (C). This compound is well known for its cytostatic activity: see for example Dalton et al. *Aust J. Chem*. 1967, 20, 2715; Svoboda et al. *J. Pharm. Sci*. 1968, 57, 1720.

Carba analogues of (C) have been synthesized resuming in an analogue, compound (D): see Boogaard, A. T.; Pandit, U. K.; Koomen, G-J. *Tetrahedron*. 1994, 50, 4811. This compound has structural similarities with the compounds of the present invention.

The structure of each of these compounds is shown on the following page.

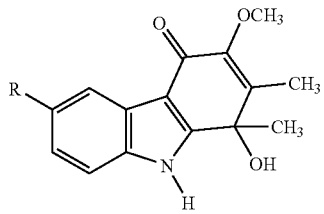

(A) Carbazomycin G, R = H
(B) Crabazomycin H, R = OCH$_3$

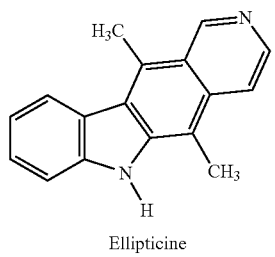

Ellipticine

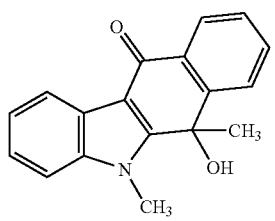

SUMMARY OF THE INVENTION

The compounds of the present invention possess a distinctive functionality in that the central ring nitrogen atom is bonded directly to an oxygen atom. Compounds of this type having such a functional group have not previously been disclosed in the prior art.

Furthermore, certain preferred compounds of the present invention possess alkanoyl (particularly formyl) and hydroxyl substituents on the same ring carbon atoms.

Thus, in a first aspect, the invention provides compounds of formula (I):

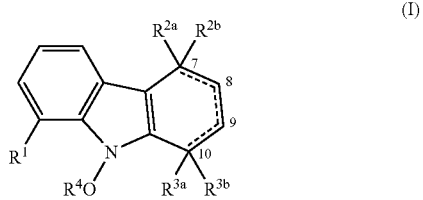

wherein:

the dotted line represents an optional double bond, with the proviso that at least one single bond is present between C7 and C10;

$R^1$ is selected from hydrogen, $C_{1-12}$ alkyl (which may be optionally substituted by a group selected from hydroxy, $C_{1-12}$ alkoxy, $C_{1-30}$ alkanoyloxy, optionally substituted $C_{7-11}$ aroyloxy, optionally substituted $C_{8-16}$ aralkanoyloxy, halogen, optionally substituted $C_{6-10}$ aryl, amino, mono-($C_{1-12}$ alkyl)amino and di-($C_{1-12}$ alkyl)amino), optionally substituted $C_{6-10}$ aryl, carboxy, $C_{1-30}$ alkoxycarbonyl, optionally substituted $C_{7-11}$ aryloxycarbonyl, optionally substituted $C_{8-16}$ aralkyloxycarbonyl, carbamoyl, N—($C_{1-12}$ alkyl)carbamoyl and N,N-di-($C_{1-12}$ alkyl)carbamoyl;

$R^{2a}$ and $R^{2b}$ are independently selected from hydrogen, hydroxy, $C_{1-12}$ alkyl, $C_{1-30}$ alkanoyl, optionally substituted $C_{7-11}$ aroyl, optionally substituted $C_{8-16}$ aralkanoyl, $C_{1-12}$ alkoxy, $C_{1-30}$ alkanoyloxy, optionally substituted $C_{7-11}$ aroyloxy and optionally substituted $C_{8-16}$ aralkanoyloxy, with the proviso that the substituent $R^{2b}$ is absent if a double bond is present between C7 and C8;

or $R^{2a}$ and $R^{2b}$ together represent oxygen;

$R^{3a}$ and $R^{3b}$ are independently selected from hydrogen, halogen, hydroxy, amino, mono-($C_{1-12}$ alkyl)amino, di-($C_{1-12}$ alkyl)amino, $C_{1-12}$ alkoxy, $C_{1-30}$ alkanoyloxy, optionally substituted $C_{7-11}$ aroyloxy, optionally substituted C8–16 aralkanoyloxy, $C_{1-12}$ alkyl (which may be optionally substituted by a group selected from hydroxy, $C_{1-12}$ alkoxy, $C_{1-30}$ alkanoyloxy, optionally substituted $C_{7-11}$ aroyloxy, optionally substituted $C_{8-16}$ aralkanoyloxy, halogen, optionally substituted $C_{6-10}$ aryl, amino, mono-($C_{1-12}$ alkyl)amino and di-($C_{1-12}$ alkyl)amino), optionally substituted $C_{6-10}$ aryl, $C_{1-30}$ alkanoyl, optionally substituted $C_{7-11}$ aroyl, optionally substituted $C_{8-16}$ aralkanoyl, carboxy, $C_{1-30}$ alkoxycarbonyl, optionally substituted $C_{7-11}$ aryloxycarbonyl, optionally substituted $C_{8-16}$ aralkyloxycarbonyl, carbamoyl, N—($C_{1-12}$ alkyl)carbamoyl and N,N-di-($C_{1-12}$ alkyl)carbamoyl, with the proviso that the substituent $R^{3b}$ is absent if a double bond is present between C9 and C10;

or $R^{3a}$ and $R^{3b}$ together represent oxygen; and $R^4$ is selected from hydrogen, $C_{1-12}$ alkyl, $C_{1-30}$ alkanoyl, optionally substituted $C_{7-11}$ aroyl and optionally substituted $C_{8-16}$ aralkanoyl;

and pharmaceutically acceptable salts thereof.

Compounds of formula (I) exhibit antitumoral activity. As described below, the compounds exhibit activity against a wide range of mammalian cancer cell lines.

Thus, in further aspects, the invention provides the use of a compound of formula (I) or a pharmaceutically acceptable salt thereof as a medicament, particularly the use of such a compound in the manufacture of a medicament for the treatment and prophylaxis of cancer (in particular lung cancer, prostate cancer, colon cancer and melanoma).

The invention further provides a method for the treatment or prophylaxis of cancer (in particular lung cancer, prostate cancer, colon cancer and melanoma) in a mammal (in particular a human), comprising administering to the affected individual an effective amount of a compound of formula (I) or a pharmaceutically acceptable salt thereof.

The invention further provides a method of production of a compound of formula (I), described in more detail later.

DETAILED DESCRIPTION OF PREFERRED EMBODIMENTS

In the definitions used in the present application, alkyl groups may be straight or branched chain groups and preferably have from 1 to about 12 carbon atoms, more preferably 1 to about 8 carbon atoms, still more preferably 1 to about 6 carbon atoms, and most preferably 1, 2, 3 or 4 carbon atoms. Methyl, ethyl and propyl including isopropyl are particularly preferred alkyl groups in the compounds of the present invention. As used herein, the term alkyl, unless otherwise modified, refers to both cyclic and noncyclic groups, although cyclic groups will comprise at least three carbon ring members.

The alkyl groups in the compounds of the present invention may be substituted by a number of different groups, including hydroxy, alkoxy, alkanoyloxy, aroyloxy, aralkanoyloxy, aryl, halogen, amino, monoalkylamino and dialkylamino. These groups are defined in more detail below. The number of substituents on the alkyl group is restricted only by the number of substitutable positions and by steric constraints. However, we prefer that the alkyl groups have from 1 to 3, more preferably 1 or 2, and most preferably only 1 substituent. When the substituted alkyl group is bonded to a ring, we prefer that the substituent is present on the carbon atom attached to the ring.

The aryl groups in the compounds of the present invention preferably have 6 to 10 carbon atoms in a single aromatic carbocyclic ring or two or more fused rings. Phenyl and naphthyl groups, especially the phenyl group, are preferred.

The aryl groups may optionally be substituted on the aromatic ring by one or more substituents. When more than one substituent is present, the substituents may be the same or different. The number of substituents on the aryl group is restricted only by the number of substitutable positions and by steric constraints. However, we prefer that the alkyl groups have from 1 to 5, more preferably 1 to 3, still more preferably 1 or 2, and most preferably only 1 substituent. The substituents may include alkyl, hydroxy, alkoxy, alkanoyloxy, aroyloxy, aralkanoyloxy, aryl, halogen, amino, monoalkylamino, dialkylamino, nitro and cyano groups, which are defined in more detail elsewhere in this specification.

Preferred aralkyl groups in the compounds of the present invention comprise an alkyl group having from 1 to 6 carbon atoms which is substituted with an aryl group as defined above to form an aralkyl group having a total of 7 to 16 carbon atoms. The aryl part of the aralkyl group may optionally be substituted on the aromatic ring by one or more substituents, the number and type of which is described above in relation to aryl groups. Examples of preferred alkyl groups include benzyl, phenethyl, phenylpropyl, 1-naphthylmethyl and naphthylethyl, of which the benzyl group is most preferred.

The halogen atoms in the compounds of the present invention are preferably fluorine, chlorine, bromine or iodine, of which chlorine and bromine are more preferred.

Preferred alkoxy groups in the compounds of the present invention include groups having one or more (but preferably only one) oxygen linkages and from 1 to about 12 carbon atoms, more preferably from 1 to about 8 carbon atoms, and still more preferably 1 to about 6 carbon atoms, and most preferably 1, 2, 3 or 4 carbon atoms. Preferred alkanoyl groups in the compounds of the present invention include those groups having one or more carbonyl (CO) groups and from 1 to about 30 carbon atoms, more preferably from 1 to about 12 carbon atoms, and still more preferably 1 to about 6 carbon atoms (including the carbonyl carbon). Alkanoyl groups having 1, 2, 3 or 4 carbon atoms, especially the formyl, acetyl, propionyl, butyryl and isobutyryl groups, are preferred and the formyl and acetyl groups especially preferred.

Preferred aroyl groups in the compounds of the present invention include those groups having one or more (but preferably only one) carbonyl (CO) groups bonded to an aryl group (defined above) to complete an aroyl group having a total of from 7 to 11 carbon atoms. The aryl part of the aroyl group may optionally be substituted by one or more substituents, the preferred number and type of which is described above in relation to aryl groups. Examples of preferred aroyl groups include benzoyl and naphthoyl, of which the benzoyl group is most preferred.

Preferred aralkanoyl groups in the compounds of the present invention include those groups having one or more (but preferably only one) carbonyl (CO) groups bonded to the alkyl part of an aralkyl group (defined above) to complete an aralkanoyl group having a total of from 8 to 16 carbon atoms. The aryl part of the aralkanoyl group may optionally be substituted by one or more substituents, the preferred number and type of which is described above in relation to aryl groups. Examples of preferred aralkanoyl groups include phenylacetyl, 3-phenylpropionyl, 4-phenylbutyryl and naphthylacetyl, of which the phenylacetyl group is most preferred.

Preferred alkanoyloxy groups in the compounds of the present invention include those groups having one or more carbonyloxy groups and from 1 to about 30 carbon atoms, more preferably from 1 to about 12 carbon atoms, and still more preferably 1 to about 6 carbon atoms (including the carbonyl carbon). When the term "alkanoyloxy" is used, it is to be understood that the group is attached to the rest of the molecule via the oxygen atom. Alkanoyloxy groups having 1, 2, 3 or 4 carbon atoms, especially the formyloxy, acetoxy, propionyloxy, butyryloxy and isobutyryloxy groups, are preferred and the formyloxy and acetyloxy groups especially preferred.

Preferred aroyloxy groups in the compounds of the present invention include those groups having one or more (but preferably only one) carbonyloxy (COO) groups wherein the carbonyl carbon is bonded to an aryl group (defined above) and the oxygen atom is attached to the remainder of the molecule. The aroyloxy group preferably has a total of from 7 to 11 carbon atoms (including the carbonyl carbon). The aryl part of the aroyloxy group may optionally be substituted by one or more substituents, the preferred number and type of which is described above in relation to aryl groups. Examples of preferred aroyloxy groups include benzoyloxy and naphthoyloxy, of which the benzoyloxy group is most preferred.

Preferred aralkanoyloxy groups in the compounds of the present invention include those groups having one or more (but preferably only one) carbonyloxy (COO) groups wherein the carbonyl carbon is bonded to the alkyl part of an aralkyl group (defined above) and the oxygen atom is attached to the remainder of the molecule. The aralkanoyloxy group has a total of from 8 to 16 carbon atoms (including the carbonyl carbon). The aryl part of the aralkanoyloxy group may optionally be substituted by one or more substituents, the preferred number and type of which is described above in relation to aryl groups. Examples of preferred aralkanoyloxy groups include phenylacetoxy, 3-phenylpropionyloxy, 4-phenylbutyryloxy and naphthylacetoxy, of which the phenylacetoxy group is most preferred.

Preferred N-alkylcarbamoyl groups in the compounds of the present invention comprise a —CO—NH— linkage (the group being attached to the rest of the molecule via the carbonyl carbon) wherein the nitrogen atom is substituted with an alkyl group having from 1 to about 12 carbon atoms, more preferably 1 to about 6 carbon atoms. N-Alkylcarbamoyl groups having 1, 2, 3 or 4 carbon atoms, especially the N-methylcarbamoyl, N-ethylcarbamoyl, N-propylcarbamoyl and N-butylcarbamoyl groups, are particularly preferred.

Preferred dialkylcarbamoyl groups in the compounds of the present invention comprise a —CO—N— linkage (the group being attached to the rest of the molecule via the carbonyl carbon) wherein the nitrogen atom is substituted with two alkyl groups, each having from 1 to about 12 carbon atoms, more preferably 1 to about 6 carbon atoms. The alkyl groups may be the same or different. N,N-Dialkylcarbamoyl groups wherein each alkyl group has 1, 2, 3 or 4 carbon atoms, especially the N,N-dimethylcarbamoyl, N,N-diethylcarbamoyl, N-methyl-N-ethylcarbamoyl, N-ethyl-N-propylcarbamoyl, N,N-dipropylcarbamoyl, N,N-dibutylcarbamoyl and N-methyl-N-butylcarbamoyl groups, are particularly preferred.

Preferred monoalkylamino groups in the compounds of the present invention have one or more (but preferably only one) NH linkages and from 1 to about 12 carbon atoms, more preferably from 1 to about 8 carbon atoms, and still more preferably 1 to about 6 carbon atoms. Alkylamino groups having 1, 2, 3 or 4 carbon atoms, especially the methylamino, ethylamino, propylamino and butylamino groups, are particularly preferred.

Preferred dialkylamino groups in the compounds of the present invention have one or more (but preferably only one) nitrogen atom bonded to two alkyl groups, each of which may from 1 to about 12 carbon atoms, more preferably from 1 to about 8 carbon atoms, and still more preferably 1 to about 6 carbon atoms. The alkyl groups may be the same or different. Dialkylamino groups wherein each alkyl group has 1, 2, 3 or 4 carbon atoms, especially the dimethylamino, diethylamino, N-methylethylamino, N-ethylpropylamino, dipropylamino, dibutylamino and N-methylbutylamino groups, are particularly preferred.

Preferred alkoxycarbonyl groups in the compounds of the present invention include those groups having one or more (but preferably only one) oxycarbonyl groups and from 1 to about 30 carbon atoms, more preferably from 1 to about 12 carbon atoms, and still more preferably 1 to about 6 carbon atoms (including the carbonyl carbon). When the term "alkoxycarbonyl"is used, it is to be understood that the group is attached to the rest of the molecule via the carbonyl carbon. Alkoxycarbonyl groups having 1, 2, 3 or 4 carbon atoms, especially the methoxycarbonyl, ethoxycarbonyl, propoxycarbonyl and butoxycarbonyl are preferred and the methoxycarbonyl and ethoxycarbonyl groups especially preferred.

Preferred aryloxycarbonyl groups in the compounds of the present invention have one or more (but preferably only one) oxycarbonyl groups wherein the carbonyl carbon is attached to the rest of the molecule and the oxygen atom is bonded to an aryl group (as defined above). The aryloxycarbonyl group preferably has a total of from 7 to 11 carbon atoms (including the carbonyl carbon). The aryl part of the aryloxycarbonyl group may optionally be substituted by one or more substituents, the preferred number and type of which is described above in relation to aryl groups. Examples of preferred aryloxycarbonyl groups include phenoxycarbonyl and naphthyloxycarbonyl, of which the phenoxycarbonyl group is most preferred.

Preferred aralkyloxycarbonyl groups in the compounds of the present invention have one or more (but preferably only one) oxycarbonyl groups wherein the carbonyl carbon is attached to the rest of the molecule and the oxygen atom is bonded to the alkyl part of an aralkyl group (defined above). The aralkyloxycarbonyl group has a total of from 8 to 16 carbon atoms (including the carbonyl carbon). The aryl part of the aralkyloxycarbonyl group may optionally be substituted by one or more substituents, the preferred number and type of which is described above in relation to aryl groups. Examples of preferred aralkyloxycarbonyl groups include benzyloxycarbonyl, phenethyloxycarbonyl and naphthylmethyloxycarbonyl, of which the benzyloxycarbonyl group is most preferred.

Preferably $R^1$ is selected from carboxy, $C_{1-12}$ alkoxycarbonyl, carbamoyl, N—($C_{1-6}$ alkyl)carbamoyl and N,N-di-($C_{1-6}$ alkyl)carbamoyl. More preferably, $R^1$ is selected from carboxy and $C_{1-6}$ alkoxycarbonyl. Still more preferably, $R^1$ is $C_{1-4}$ alkoxycarbonyl. In a particularly preferred embodiment, $R^1$ is methoxycarbonyl.

Preferably $R^{2a}$ and $R^{2b}$ are independently selected from hydrogen, hydroxy, $C_{1-6}$ alkoxy and $C_{1-12}$ alkanoyloxy, or $R^{2a}$ and $R^{2b}$ together represent oxygen. More preferably, $R^{2a}$ and $R^{2b}$ are independently selected from hydrogen, hydroxy and $C_{1-4}$ alkoxy, or $R^{2a}$ and $R^{2b}$ together represent oxygen. It is particularly preferred that $R^{2a}$ and $R^{2b}$ together represent oxygen.

Preferably $R^{3a}$ and $R^{3b}$ are independently selected from hydrogen, hydroxy, $C_{1-6}$ alkoxy, $C_{1-12}$ alkanoyloxy, $C_{1-6}$ alkyl (which may be optionally substituted by a group selected from hydroxy, $C_{1-6}$ alkoxy and $C_{1-12}$ alkanoyloxy), $C_{1-12}$ alkanoyl, carboxy and $C_{1-12}$ alkoxycarbonyl; or $R^{3a}$ and $R^{3b}$ together represent oxygen. More preferably, $R^{3a}$ and $R^{3b}$ are independently selected from hydrogen, hydroxy, $C_{1-4}$ alkyl (which is substituted by a group selected from hydroxy and $C_{1-4}$ alkoxy), $C_{1-6}$ alkanoyl, carboxy and $C_{1-6}$ alkoxycarbonyl. Even more preferably, $R^{3a}$ and $R^{3b}$ are independently selected from hydroxy, hydroxymethyl, $C_{1-4}$ alkanoyl and carboxy. It is particularly preferred that one of $R^{3a}$ and $R^{3b}$ is hydroxy and the other is formyl.

It is preferred that a double bond is present between C8 and C9. However, in alternative embodiments, double bonds are present between C7 and C8 and between C9 and C10 (so as to make the ring including C7, C8, C9 and C10 aromatic).

As the person skilled in the art will readily appreciate, the preferred definitions of $R^1$, $R^2$, $R^3$, $R^4$ and the dotted line may be combined in various ways, and the compounds covered by all such combinations and permutations of the above preferred definitions are to be considered as being part of this invention. A combination of two preferred definitions is more preferred, a combination of three preferred definitions is even more preferred, a combination of four preferred definitions is still more preferred and a combination of all five preferred definitions is especially preferred.

The most preferred compound of this invention is 8-formyl-8,9-dihydroxy-5-oxo-8,9-dihydro-5H-carbazole-1-carboxylic acid methyl ester (coproverdine).

Some of the compounds of formula (I) contain a basic group (such as an amino group), and may therefore form a salt. The nature of such salts is not critical to the present invention, provided that, when the compound is used for therapeutic purposes, the salts are pharmaceutically acceptable, ie more pharmaceutically active, about as pharmaceutically active or not unduly less pharmaceutically active than the free base compound, and less toxic, about as toxic or not unduly more toxic than the free base compound. This can easily be ascertained by simple tests readily apparent to those skilled in the art. However, when the compound is used for other purposes (for example, as an intermediate in the preparation of another compound) even this restriction does not apply. Examples of suitable salts include inorganic acid salts such as hydrofluoride, hydrochloride, hydrobromide, hydroiodide, sulfate and phosphate; carboxylic acid salts such as acetate, benzoate, oxalate, maleate, fumarate, tartrate, citrate and succinate; and sulfonic acid salts such as methanesulfonate, benzenesulfonate and p-toluenesulfonate. Preferred salts include hydrochloride, hydrobromide, tartrate and succinate.

Some of the compounds of formula (I) have acidic groups, such as a phenolic hydroxyl group or a carboxy group, and may therefore form a salt by combination with a metal ion. The nature of such salts is not critical to the present invention, provided that, when the compound is used for therapeutic purposes, the salts are pharmaceutically acceptable, ie more pharmaceutically active, about as pharmaceutically active or not unduly less pharmaceutically active than the free acid compound, and less toxic, about as toxic or not unduly more toxic than the free acid compound. This can easily be ascertained by simple tests readily apparent to those skilled in the art. However, when the compound is used for other purposes (for example, as an intermediate in the preparation of another compound) even this restriction does not apply. A salt of such a compound can be prepared by a conventional method. Examples of the salt include alkali metal salts such as lithium, sodium and potassium salts; alkaline earth metal salts such as calcium, barium and magnesium salts; salts of other metals such as an aluminium and iron salts; ammonium salts; and organic amine salts such as methylamine and triethylamine salts.

Certain compounds of formula (I) have asymmetric carbon atoms, and different stereoisomers (both enantiomers and diastereomers) of such compounds can therefore exist. The present invention encompasses each pure stereoisomer and a mixture of the isomers in any ratio. A pure enantiomer of the compound of formula (I) can, for example, be synthesized from an optically active starting material or can be obtained from a mixture of enantiomers of compounds of formula (I) via a conventional optical resolution technique.

The most preferred compound of the present invention (coproverdine) may be prepared by isolating it from a natural source, in particular from an ascidian. Conveniently, the compound may be isolated by extraction using a suitable solvent. The solvent may preferably be an organic solvent: for example, an aliphatic hydrocarbon such as hexane, heptane, ligroin or petroleum ether; an aromatic hydrocarbon such as benzene, toluene or xylene; a halogeno-hydrocarbon such as dichloromethane, chloroform, carbon tetrachloride, dichloroethane, chlorobenzene or dichlorobenzene; an ether such as diethyl ether, diisopropyl ether, tetrahydrofuran, dioxane, dimethoxyethane or diethylene glycol dimethyl ether; an alcohol such as methanol, ethanol or isopropanol; a ketone such as acetone, methyl ethyl ketone, methyl isobutyl ketone, isophorone or cyclohexanone; an amide such as formamide, dimethylformamide, dimethylacetamide, N-methyl-2-pyrrolidone or hexamethylphosphoric triamide; a sulfoxide such as dimethylsulfoxide; or a sulfone such as sulfolane; or mixtures thereof. The solvent is preferably a mixture of dichloromethane and methanol.

The compound may then be further purified by purification techniques known to those skilled in the art, for example recrystallisation (for solid compounds) or chromatographic techniques such as column chromatography, liquid chromatography or gas chromatography, in particular liquid chromatography techniques such as reversed-phase liquid chromatography, vacuum liquid chromatography and/or gel permeation chromatography.

The compounds of the present invention other than coproverdine may be prepared by derivatising coproverdine. The compound may undergo multiple transformations to produce a wide range of possible derivatives. The nature of such derivatisations will be readily apparent to those skilled in the art.

For example, a compound of formula (I) wherein $R^1$ is a carboxy group may be prepared from coproverdine by hydrolysis of the methyl ester group. The hydrolysis may be catalysed by acid or base and may be achieved, for example, by treating coproverdine with aqueous acid or base, for example aqueous hydrochloric acid or aqueous sodium hydroxide.

A compound of formula (I) wherein $R^1$ is an alkoxycarbonyl group (other than a methoxycarbonyl group), an aryloxycarbonyl group or an aralkyloxycarbonyl group may be prepared from coproverdine by replacement of the methyl ester group with an alternative ester group. This may conveniently be achieved by treating coproverdine with a suitable alcohol or alkoxide derivative in a transesterification reaction. The transesterification reaction may preferably be catalysed by acid or base.

Similarly, a compound of formula (I) wherein $R^1$ is a carbamoyl, monoalkylcarbamoyl or dialkylcarbamoyl group may be prepared from coproverdine by replacement of the methyl ester group with an amide group. Such a transformation may be achieved, for example, by treating coproverdine with ammonia, a suitable mono- or dialkylamine or a salt thereof.

A compound of formula (I) wherein $R^1$ is a hydroxymethyl group may be prepared from coproverdine (or from a compound wherein $R^1$ is another alkoxycarbonyl group, an aryloxycarbonyl group or an aralkyloxycarbonyl group) by reduction of the ester group. Any suitable agent known in the art to reduce esters may be used, examples of which include lithium aluminium hydride, diisobutylaluminium hydride, borane and triethoxysilane.

Similarly, a compound of formula (I) wherein $R^1$ is an alkyl group substituted at the carbon next to the ring with a monoalkylamino or dialkylamino group may be prepared from such a compound wherein $R^1$ is a carbamoyl, monoalkylcarbamoyl or dialkylcarbamoyl group by reduction of the amide group. Any suitable agent known in the art to reduce amides may be used, examples of which include lithium aluminium hydride, borane and trichlorosilane.

A compound of formula (I) wherein one of $R^{2a}$ and $R^{2b}$ is hydrogen and the other is hydroxy may conveniently be prepared from coproverdine by reduction of the ketone group. Any suitable agent known in the art to reduce a ketone group may be used, examples of which include lithium aluminium hydride, diisobutylaluminium hydride, sodium borohydride, sodium cyanoborohydride, borane, tributyltin hydride, lithium trimethoxyaluminium hydride, hydrogen and a metal catalyst (preferably platinum) and aluminium triisopropoxide in isopropanol.

A compound of formula (I) wherein one of $R^{2a}$ and $R^{2b}$ is hydrogen and the other is alkoxy may conveniently be prepared from a compound wherein one of $R^{2a}$ and $R^{2b}$ is hydrogen and the other is hydroxy by alkylation of the hydroxy group (or its conjugate base) with a suitable alkylating agent. Any suitable alkylating agent may be used, examples of which include alkyl halides such as methyl bromide and methyl iodide, alkyl sulfates such as dimethyl sulfate, and alkylsulfonates such as propyl p-toluenesulfonate and ethyl trifluoromethanesulfonate. The reaction may preferably be catalysed by a suitable base, examples of which include organic bases such as pyridine, N,N-dimethylaminopyridine and triethylamine and inorganic bases such as sodium hydroxide, sodium carbonate and sodium hydrogen carbonate.

Similarly, a compound of formula (I) wherein one of $R^{2a}$ and $R^{2b}$ is hydrogen and the other is alkanoyloxy, aroyloxy or aralkanoyloxy may conveniently be prepared from a compound wherein one of $R^{2a}$ and $R^{2b}$ is hydrogen and the other is hydroxy by acylation of the hydroxy group with a suitable acylating agent. Any suitable acylating agent may be used, examples of which include acid halides such as acetyl chloride, acid anhydrides such as acetic anhydride and a carboxylic acid (for example, acetic acid) in the presence of a dehydrating agent such as dicyclohexylcarbodiimide (DCC). The reaction may preferably be catalysed by a suitable base, examples of which include organic bases such as pyridine, N,N-dimethylaminopyridin and triethylamine and inorganic bases such as sodium hydroxide, sodium carbonate and sodium hydrogen carbonate.

A compound of formula (I) wherein one of $R^{3a}$ and $R^{3b}$ is hydroxy and the other is hydroxymethyl may conveniently be prepared from coproverdine by reduction of the formyl group. Any suitable agent known in the art to reduce a formyl group may be used, examples of which include lithium aluminium hydride, diisobutylaluminium hydride, sodium borohydride, sodium cyanoborohydride, borane, tributyltin hydride, lithium trimethoxyaluminium hydride, hydrogen and a metal catalyst (preferably platinum) and aluminium triisopropoxide in isopropanol.

A compound of formula (I) wherein one of $R^{3a}$ and $R^{3b}$ is methyl substituted with an alkoxy group may be prepared from a compound wherein one of $R^{3a}$ and $R^{3b}$ is hydroxymethyl by alkylation of the hydroxy group (or its conjugate base) with a suitable alkylating agent. Any suitable alkylating agent may be used, examples of which are described and exemplified above in relation to the transformations involving the groups $R^{2a}$ and $R^{2b}$. The reaction may preferably be catalysed by a suitable base, examples of which are described and exemplified above in relation to the transformations involving the groups $R^{2a}$ and $R^{2b}$.

Similarly, a compound of formula (I) wherein one of $R^{3a}$ and $R^{3b}$ is methyl substituted with an alkanoyloxy, aroyloxy or aralkanoyloxy group may be prepared from a compound wherein one of $R^{3a}$ and $R^{3b}$ is hydroxymethyl by acylation of the hydroxy group (or its conjugate base) with a suitable acylating agent. Any suitable acylating agent may be used, examples of which are described and exemplified above in relation to the transformations involving the groups $R^{2a}$ and $R^{2b}$. The reaction may preferably be catalysed by a suitable base, examples of which include organic bases such as pyridine, N,N-dimethylaminopyridine and triethylamine and inorganic bases such as sodium hydroxide, sodium carbonate and sodium hydrogen carbonate.

A compound of formula (I) wherein one of $R^{3a}$ and $R^{3b}$ is carboxy may be conveniently be prepared from coproverdine by oxidation of the formyl group. Any agent suitable for oxidising an aldehyde group may be employed, examples of which include potassium dichromate, chromium trioxide in sulfuric acid, nitric acid and potassium permanganate.

A compound of formula (I) wherein one of $R^{3a}$ and $R^{3b}$ is an alkoxycarbonyl group, an aryloxycarbonyl group or an aralkyloxycarbonyl group may be prepared from a compound wherein one of $R^{3a}$ and $R^{3b}$ is carboxy by esterification of the carboxylic acid group. This may be achieved by any convenient means known in the art. For example, the starting compound may be treated directly with a suitable alcohol in the presence of acid. Alternatively the carboxy group may first be converted to a more reactive derivative (such as an acid halide or acid anhydride) by treatment with a suitable reagent, eg oxalyl chloride, phosphorus trichloride or acetic anhydride, followed by treatment with a suitable alcohol. The reaction(s) may preferably be catalysed by a suitable base, examples of which are described and exemplified above in relation to the transformations involving the groups $R^{2a}$ and $R^{2b}$.

Similarly, a compound of formula (I) wherein one of $R^{3a}$ and $R^{3b}$ is a carbamoyl, monoalkylcarbamoyl or dialkylcarbamoyl group may be prepared from a compound of formula (I) wherein one of $R^{3a}$ and $R^{3b}$ is carboxy by treating the starting compound with ammonia, a suitable mono- or dialkylamine or a salt thereof. The compound may be treated directly with the starting reagent or the carboxy group may first be converted to a more reactive derivative as described above.

A compound of formula (I) wherein $R^4$ is alkyl may conveniently be prepared from coproverdine by alkylation of the hydroxy group (or its conjugate base) with a suitable alkylating agent. Any suitable alkylating agent may be used, examples of which are described and exemplified above in relation to the transformations involving the groups $R^{2a}$ and $R^{2b}$. The reaction may preferably be catalysed by a suitable base, examples of which are described and exemplified above in relation to the transformations involving the groups $R^{2a}$ and $R^{2b}$.

Similarly, a compound of formula (I) wherein $R^4$ is alkanoyl, aroyl or aralkanoyl may conveniently be prepared from coproverdine by acylation of the hydroxy group with a suitable acylating agent. Any suitable acylating agent may be used, examples of which are described and exemplified above in relation to the transformations involving the groups $R^{2a}$ and $R^{2b}$. The reaction may preferably be catalysed by a suitable base, examples of which include organic bases such as pyridine, N,N-dimethylaminopyridine and triethylamine and inorganic bases such as sodium hydroxide, sodium carbonate and sodium hydrogen carbonate.

When coproverdine is treated with certain reducing agents, both the oxo group $R^{2a}/R^{2b}$ and the formyl group $R^{3b}$ may be simultaneously reduced to give a compound wherein $R^{2a}$ is hydrogen, $R^{2b}$ is hydroxy and $R^{3b}$ is a hydroxymethyl group.

When coproverdine is reduced to give a compound wherein one of $R^{2a}$ and $R^{2b}$ is hydrogen and one of $R^{3a}$ and $R^{3b}$ is hydroxy, the compound may lose a molecule of water to form a compound wherein double bonds are present between C7 and C8 and between C9 and C10. An example of this process is shown below:

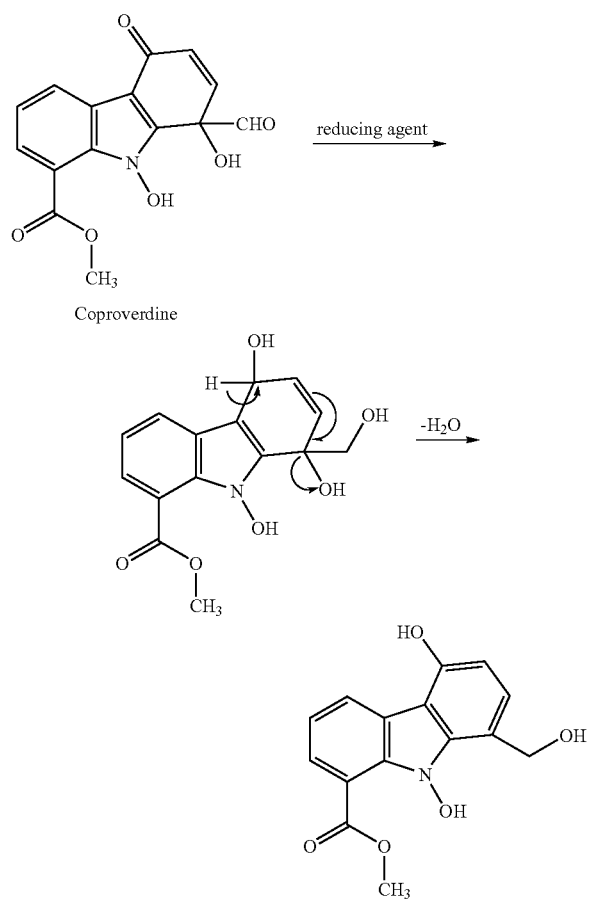

The present invention also relates to pharmaceutical preparations, which contain as active ingredient a compound or compounds of the invention, as well as the processes for their preparation.

Examples of pharmaceutical compositions include any solid (tablets, pills, capsules, granules, etc.) or liquid (solutions, suspensions or emulsions) with suitable composition or oral, topical or parenteral administration, and they may contain the pure compound or in combination with any carrier or other pharmacologically active compounds. These compositions may need to be sterile when administered parenterally.

Administration of the compounds or compositions of the present invention may be by any suitable method, such as intravenous infusion, oral preparations, intraperitoneal and intravenous administration. We prefer that infusion times of up to 24 hours are used, more preferably 2–12 hours, with 2–6 hours most preferred. Short infusion times which allow treatment to be carried out without an overnight stay in hospital are especially desirable. However, infusion may be 12 to 24 hours or even longer if required. Infusion may be carried out at suitable intervals of say 2 to 4 weeks. Pharmaceutical compositions containing compounds of the invention may be delivered by liposome or nanosphere encapsulation, in sustained release formulations or by other standard delivery means.

The correct dosage of the compounds will vary according to the particular formulation, the mode of application, and the particular situs, host and tumour being treated. Other factors like age, body weight, sex, diet, time of administration, rate of excretion, condition of the host, drug combinations, reaction sensitivities and severity of the disease shall be taken into account. Administration can be carried out continuously or periodically within the maximum tolerated dose.

The compounds and compositions of this invention may be used with other drugs to provide a combination therapy. The other drugs may form part of the same composition, or be provided as a separate composition for administration at the same time or a different time. The identity of the other drug is not particularly limited, and suitable candidates include:

a) drugs with antimitotic effects, especially those which target cytoskeletal elements, including microtubule modulators such as taxane drugs (such as taxol, paclitaxel, taxotere, docetaxel), podophylotoxins or vinca alkaloids (vincristine, vinblastine);

b) antimetabolite drugs such as 5-fluorouracil, cytarabine, gemcitabine, purine analogues such as pentostatin, methotrexate);

c) alkylating agents such as nitrogen mustards (such as cyclophosphamide or ifosphamide);

d) drugs which target DNA such as the antracycline drugs adriamycin, doxorubicin, pharmorubicin or epirubicin;

e) drugs which target topoisomerases such as etoposide;

f) hormones and hormone agonists or antagonists such as estrogens, antiestrogens (tamoxifen and related compounds) and androgens, flutamide, leuprorelin, goserelin, cyprotrone or octreotide;

g) drugs which target signal transduction in tumour cells including antibody derivatives such as herceptin;

h) alkylating drugs such as platinum drugs (cis-platin, carbonplatin, oxaliplatin, paraplatin) or nitrosoureas;

i) drugs potentially affecting metastasis of tumours such as matrix metalloproteinase inhibitors;

j) gene therapy and antisense agents;

k) antibody therapeutics;

l) other bioactive compounds of marine origin, notably the did mnins such as aplidine;

m) steroid analogues, in particular dexamethasone;

n) anti-inflammatory drugs, in particular dexamethasone; and o) anti-emetic drugs, in particular dexamethasone.

EXAMPLES

The following Examples illustrate the present invention but do not limit the scope thereof.

Example 1

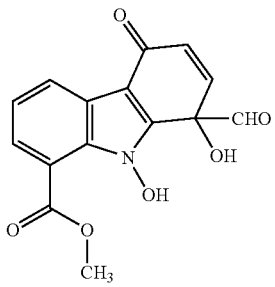

8-formyl-8,9-dihydroxy-5-oxo-8,9-dihydro-5H-carbazole-1-carboxylic acid methyl ester (coproverdine)

A specimen of a rare, unidentified ascidian was collected from Irishman's Garden at Three Kings (55 km offshore from the Northern tip of the North Island, New Zealand). Collection was by SCUBA at a depth of 20–25 m from inside a cave in March 1997. The specimen was described as epizoic on an Anchorina sponge. A voucher specimen is stored in the museum at NIWA, Wellington, New Zealand (NIWA code MNP670). The specimen is thought to be a polycitorid, possibly a *Eudistoma* sp.

The frozen specimen (34 g) was exhaustively extracted with MeOH/DCM (3:1; 700 mL), filtered through a pad of Celite® and the extract (1.4 g) subjected to C18 vacuum liquid chromatography, followed by gel permeation chromatography on Sephadex® LH-20 eluting with MeOH.

The product was further purified using reversed-phase HPLC (4 mL/min flow rate) using a $CH_3CN/H_2O$ gradient (30% to 75%) over 30 minutes on a Phenomenex Prodigy® 5μ ODS column (100 Å; 250×10 mm) with UV detection at 254 nm to yield the title compound.

Apperance: yellow oil.

Optical rotation $[\alpha]^{20}_D$ –8° (c 0.36, EtOH).

IR spectrum ($CHCl_3$) $v_{max}/cm^{-1}$: 3690 (sharp), 3500 (broad), 1665, 1603, 1556, 1290.

UV spectrum (EtOH) $\lambda_{max}/nm$ ($\epsilon$) 208 (20000), 270 (6700), 302 (4800), 382 (16000)

$^1$H NMR spectrum ($CD_3OD$, 300 MHz): See Table 1.

$^{13}$C NMR data ($CD_3OD$, 75 MHz): See Table 1.

Mass spectrum (EI, 70 eV) m/z 301 ($M^+$, 35), 285 (75), 273 (24), 253 (48), 225 (100), 213 (28), 197 (26), 169 (28), 146 (20).

High Resolution Fast Atom Bombardment mass spectrum m/z 302.0673 ($[MH]^+$, calculated for $C_{15}H_{12}NO_6$, 302.0665).

TABLE 1

NMR Data for Coproverdine

| No. | $^{13}C^b$ | $^1H$ δ [m, J (Hz)]$^c$ | gCOSY | gHMBC$^d$ |
|---|---|---|---|---|
| 1 | 90.5 | — | — | — |
| 2 | 143.6 | 7.01 (d, J = 10.2) | H 3 | C1, C4, C9a, C10$^e$ |
| 3 | 128.5 | 6.25 (d, J = 10.2) | H 2 | C1, C2, C4, C4a, C10$^e$ |
| 4 | 186.6 | — | — | — |
| 4a | 105.7 | — | — | — |
| 4b | 127.7 | — | — | — |
| 5 | 125.1 | 7.39 (dd, J = 1.5, 8.0) | H 6 | C4a$^e$, C4b, C6, C8a |
| 6 | 126.4 | 7.28 (dd, J = 8.0, 8.0) | H 5, H 7 | C4b, C5, C7, C8, C8a |
| 7 | 125.9 | 7.84 (dd, J = 1.5, 8.0) | H 6 | C4b, C5; C6, C8, C8a$^e$, C11 |
| 8 | 118.3 | — | — | — |
| 8a | 144.9 | — | — | — |
| 9 | — | — | — | — |
| 9a | 157.2 | — | — | — |
| 10 | 192.7 | 10.13 (s) | — | C1, C4a, C9a |
| 11 | 168.2 | — | — | — |
| 12 | 53.4 | 4.06 (s) | — | C11 |
| 1-OH | — | 8.50 (bs)$^f$ | — | — |
| 9-OH | — | 8.50 (bs)$^f$ | — | — |

$^a$Spectra were recorded in $CD_3OD$.
$^{b\,13}$C NMR at 75 MHz, referenced to $CD_3OD$ (δ 49.3) and assignments are supported by a gHSQC NMR experiment
$^c\,^1$H NMR at 300 MHz and 500 MHz, referenced to residual solvent $CH_2OD$ (δ 3.3).
$^d$gHMBC NMR experiments were run using J = 140 and 160 Hz and $J_{nxh}$ = 2, 4, 8, 9, 10 Hz.
$^e$These HMBC correlations were weak.
$^f$This signal may be interchanged.

Example 2

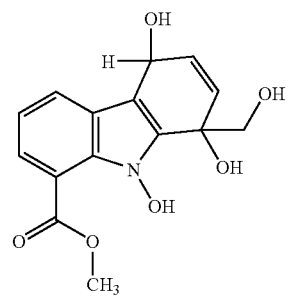

(2a)

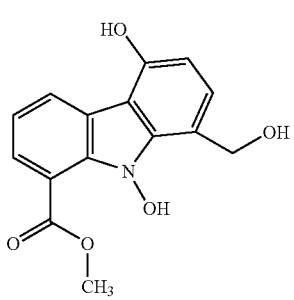

(2b)

A mixture of coproverdine (0.2 mg) (obtained as described in Example 1 above) and $NaBH_4$ (3.5 mg) in dry methanol (3 mL) were stirred at room temperature for 2 hours. The reaction mixture was concentrated under reduced pressure and re-dissolved in methanol (2 mL). The solution was analysed by reversed phase HPLC and mass spectrometry. HPLC analysis indicated the presence of two compounds which were more polar than coproverdine, but with the same UV profile. These compounds are believed to be compounds (2a) and (2b).

Low resolution ESIMS (+ve) (30 V) for compound (2a): m/z 288.21 [MH]$^+$; calculated for $C_{15}H_{13}NO_5$: 287.2675.

Biological Activity

Biological tests were carried out on coproverdine (the compound of Example 1 of the present application). A colorimetric type of assay, using sulforhodamine B (SRB) reaction, was used to provide a quantitative measurement of cell growth and viability. The technique described by Skehan, et al., *J Natl. Cancer Inst.*, 1990, 82, 1107, was followed. The reader is also referred to the following references:

Faircloth et al. *Journal of Tissue and Culture Methods*, 1988, 11, 201.

Monks et al. *Articles*, 1991, 83, 757.

Mosmann et al. *Journal of Immunological Methods*, 1983, 65, 55.

The tests gave an $IC_{50}$ result of 950 ng/mL against th P388 leukemia cell line.

Further biological tests were carried out on coproverdine using similar methods. The results are given using the following cellular response parameters: GI=growth inhibition, TGI=total growth inhibition (cytostatic effect) and LC=cell killing (cytotoxic effect).

The results are shown in Table 2 below.

TABLE 2

In vitro AT activity of coproverdine

| Cell lines | 24 wells/16 mm 10,000 cells/72 h | 96 wells/9 mm 5,000 cells/48 h | | |
|---|---|---|---|---|
| | $IC_{50}$ (µM) | $GI_{50}$ (µM) | TGI (µM) | $LC_{50}$ (µM) |
| Leukemia (P-388) | 1.6 | nd | nd | nd |
| Lung (A-549) | 0.3 | 7 | 15 | 50 |
| Colon (HT-29) | 0.3 | 6 | 16 | 50 |
| Melanoma (MEL-28) | 0.3 | nd | nd | nd |
| Prostate (DU-145) | 0.3 | nd | nd | nd |

$IC_{50}$: Concentration that causes 50% growth inhibition
$GI_{50}$: Concentration that causes 50% growth inhibition with correction for cell OD at time zero
TGI: Total growth inhibition (cytostatic effect)
$LC_{50}$: Concentration that causes 50% cell killing (cytotoxic effect)
nd: Not determined

The invention claimed is:

1. A compound of formula (I):

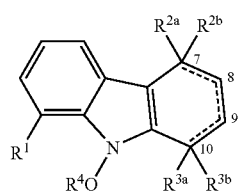

(I)

wherein:
the dotted line represents an optional double bond, with the proviso that at least one single bond is present between C7 and C10;
$R^1$ is selected from hydrogen, $C_{1-12}$ alkyl, which may be optionally substituted by a group selected from hydroxyl, $C_{1-12}$ alkoxy, $C_{1-30}$ alkanoyloxy, optionally substituted $C_{7-11}$ aroyloxy, optionally substituted $C_{8-16}$ aralkanoyloxy, halogen, optionally substituted $C_{6-10}$ aryl, amino, mono-($C_{1-12}$ alkyl)amino and di-($C_{1-12}$ alkyl)amino; optionally substituted $C_{6-10}$ aryl; carboxy; $C_{1-30}$ alkoxycarbonyl; optionally substituted $C_{7-11}$ aryloxycarbony; optionally substituted $C_{8-16}$ aralkyloxycarbonyl; carbamoyl; N—($C_{1-12}$ alkyl)carbamoyl and N,N-di-($C_{1-12}$ alkyl)carbamoyl;
$R^{2a}$ and $R^{2b}$ are independently selected from hydrogen, hydroxy, $C_{1-12}$ alkyl, $C_{1-30}$ alkanoyl, optionally substituted $C_{7-11}$ aroyl, optionally substituted $C_{8-16}$ aralkanoyl, $C_{1-12}$ alkoxy, $C_{1-30}$ alkanoyloxy, optionally substituted $C_{7-11}$ aroyloxy and optionally substituted $C_{8-16}$ aralkanoyloxy, with the proviso that the substituent $R^{2b}$ is absent if a double bond is present between C7 and C8;
or $R^{2a}$ and $R^{2b}$ together represent oxygen;
$R^{3a}$ and $R^{3b}$ are independently selected from hydrogen; halogen; hydroxy; amino; mono-($C_{1-12}$ alkyl)amino; di-($C_{1-12}$ alkyl)amino; $C_{1-12}$ alkoxy; $C_{1-30}$ alkanoyoxyl; optionally substituted $C_{7-11}$ aroyloxy; optionally substituted $C_{8-16}$ aralkanoyloxy; $C_{1-12}$ alkyl, which may be optionally substituted by a group selected from hydroxy, $C_{1-12}$ alkoxy, $C_{1-30}$ alkanoyloxy, optionally substituted $C_{7-11}$ aroyloxy, optionally substituted $C_{8-16}$ aralkanoyloxy, halogen, optionally substituted $C_{6-10}$, aryl, amino, mono-($C_{1-12}$alkyl)amino and di-($C_{1-12}$ alkyl)amino; optionally substituted $C_{6-10}$ aryl; $C_{1-30}$ alkanoyl, optionally substituted $C_{7-11}$ aroyl; optionally substituted $C_{8-16}$ aralkanoyl; carboxy; $C_{1-30}$ alkoxycarbonyl; optionally substituted $C_{7-11}$ aryloxycarbonyl; optionally substituted $C_{8-16}$ aralkyloxycarbonyl; carbamoyl; N—($C_{1-12}$ alkyl) carbamoyl and N,N-di-($C_{1-12}$ alkyl) carbamoyl, with the proviso that the substituent $R^{3b}$ is absent if a double bond is present between C9 and C10;
or $R^{3a}$ and $R^{3b}$ together represent oxygen; and
$R^4$ is selected from hydrogen, unsubstituted $C_{1-12}$ alkyl, $C_{1-30}$ alkanoyl, optionally substituted $C_{7-11}$ aroyl and optionally substituted $C_{8-16}$ aralkanoyl;
or a pharmaceutically acceptable salt thereof, with the exception of the following compounds:
(a) a compound wherein $R^1$ is hydrogen or halogen, $R^{2a}$, $R^{2b}$, $R^{3a}$ and $R^{3b}$ are all hydrogen, $R^4$ is hydrogen or lower alkyl, and double bonds are present between C7 and C8 and between C9 and C10;
(b) a compound wherein $R^1$, $R^{2a}$, $R^{2b}$, $R^{3a}$ and $R^{3b}$ are all hydrogen, $R^4$ is methyl, and double bonds are present between C7 and C8 and between C9 and C10; and
(c) a compound wherein $R^1$, $R^{2a}$, $R^{2b}$, $R^{3a}$, $R^{3b}$ and $R^4$ are all hydrogen, and no double bonds are present between C7 and C10.

2. A compound according to claim 1, wherein $R^1$ is selected from carboxy, $C_{1-12}$ alkoxycarbonyl, carbamoyl, N—($C_{1-6}$ alkyl) carbamoyl and N,N-di-($C_{1-6}$ alkyl) carbamoyl.

3. A compound according to claim 1, wherein $R^1$ is selected from carboxy and $C_{1-6}$ alkoxycarbonyl.

4. A compound according to claim 1, wherein $R^1$ is $C_{1-4}$ alkoxycarbonyl.

5. A compound according to claim 1, wherein $R^1$ is methoxycarbonyl.

6. A compound according to claim 1, wherein $R^{2a}$ and $R^{2b}$ are independently selected from hydrogen, hydroxy, $C_{1-6}$ alkoxy and $C_{1-12}$ alkanoyloxy, or $R^{2a}$ and $R^{2b}$ together represent oxygen.

7. A compound according to claim 1, wherein $R^{2a}$ and $R^{2b}$ are independently selected from hydrogen, hydroxy and $C_{1-4}$ alkoxy, or $R^{2a}$ and $R^{2b}$ together represent oxygen.

8. A compound according to claim 1, wherein $R^{2a}$ and $R^{2b}$ together represent oxygen.

9. A compound according to claim 1, wherein $R^{3a}$ and $R^{3b}$ are independently selected from hydrogen; hydroxy; $C_{1-6}$ alkoxyl; $C_{1-12}$ alkanoyloxyl; $C_{1-6}$ alkyl, which may be optionally substituted by a group selected from hydroxy, $C_{1-6}$ alkoxy and $C_{1-12}$ alkanoyloxy; $C_{1-12}$ alkanoyl; carboxy and $C_{1-12}$ alkoxycarbonyl; or $R^{3a}$ and $R^{3b}$ together represent oxygen.

10. A compound according to claim 1, wherein $R^{3a}$ and $R^{3b}$ are independently selected from hydrogen; hydroxy; $C_{1-4}$ alkyl, which is substituted by a group selected from hydroxy and $C_{1-4}$ alkoxy; $C_{1-6}$ alkanoy; carboxy and $C_{1-6}$ alkoxycarbonyl.

11. A compound according to claim 1, wherein $R^{3a}$ and $R^{3b}$ are independently selected from hydroxy, hydroxymethyl, $C_{1-4}$ alkanol and carboxy.

12. A compound according to claim 1, wherein one of $R^{3a}$ and $R^{3b}$ is hydroxy and the other is formyl.

13. A compound according to claim 1, wherein a double bond is present between C8 and C9.

14. A compound according to claim 1, wherein double bonds are present between C7 and C8 and between C9 and C10.

15. 8-formyl-8,9-dihydroxy-5-oxo-8,9-dihydro-5H-carbazole-1-carboxylic acid methyl ester, which is coproverdine, and pharmaceutically acceptable salts thereof according to claim 1.

16. A pharmaceutical preparation which contains as active ingredient a compound according to claim 1, or a pharmaceutically acceptable salt thereof.

17. A method for the treatment of lung cancer, prostate cancer, colon cancer, leukemia, or melanoma in a mammal, comprising administering to the affected individual an effective amount of a compound of formula (I):

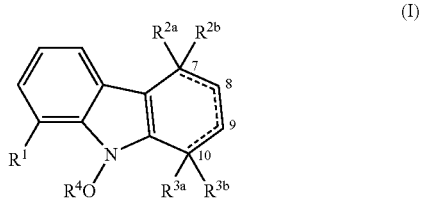

(I)

wherein
the dotted line represents an optional double bond, with the proviso that at least one single bond is present between C7 and C10;
$R^1$ is selected from hydrogen: $C_{1-12}$ alkyl, which may be optionally substituted by a group selected from hydroxyl, $C_{1-12}$ alkoxy, $C_{1-30}$ alkanoyloxy, optionally substituted $C_{7-11}$, aroyloxy, optionally substituted $C_{8-16}$ aralkanoyloxy, halogen, optionally substituted $C_{6-10}$ aryl, amino, mono-($C_{1-12}$ alkyl)amino and di-($C_{1-12}$ alkyl)amino: optionally substituted $C_{6-10}$ aryl; carboxy; $C_{1-30}$ alkoxycarbonyl; optionally substituted $C_{7-11}$ aryloxycarbonyl; optionally substituted $C_{8-16}$ aralkyloxycarbonyl; carbamoyl; N—($C_{1-12}$ alkyl)carbamoyl and N,N-di-($C_{1-12}$ alkyl)carbamoyl;
$R^{2a}$ and $R^{2b}$ are independently selected from hydrogen, hydroxy, $C_{1-12}$ alkyl, $C_{1-30}$ alkanoyl, optionally substituted $C_{7-11}$ aroyl, optionally substituted $C_{8-16}$ aralkanoyl, $C_{1-12}$ alkoxy, $C_{1-30}$ alkanoyloxy, optionally substituted $C_{7-11}$ aroyloxy and optionally substituted $C_{8-16}$ aralkanoyloxy, with the proviso that the substituent $R^{2b}$ is absent if a double bond is present between C7 and C8;
or $R^{2a}$ and $R^{2b}$ together represent oxygen;
$R^{3a}$ and $R^{3b}$ are independently selected from hydrogen; halogen; hydroxy; amino; mono-($C_{1-12}$ alkyl)amino; di-($C_{1-12}$ alkyl)amino; $C_{1-12}$ alkoxy; $C_{1-30}$ alkanoyloxy; optionally substituted $C_{7-11}$ aroyloxy, optionally substituted $C_{8-16}$ aralkanoyloxy; $C_{1-12}$ alkyl, which may be optionally substituted by a group selected from hydroxy, $C_{1-12}$ alkoxy, $C_{1-30}$ alkanoyloxy, optionally substituted $C_{7-11}$ aroyloxy, optionally substituted $C_{8-16}$ aralkanoyloxy, halogen, optionally substituted $C_{6-10}$, aryl, amino, mono-($C_{1-12}$ alkyl)amino and di-($C_{1-12}$ alkyl)amino; optionally substituted $C_{6-10}$ aryl; $C_{1-30}$ alkanoyl, optionally substituted $C_{7-11}$ aroyl; optionally substituted $C_{8-16}$ aralkanoyl; carboxy; $C_{1-30}$ alkoxycarbonyl; optionally substituted $C_{7-11}$ aryloxycarbonyl; optionally substituted $C_{8-16}$ aralkyloxycarbonyl; carbamoyl; N—($C_{1-12}$ alkyl) carbamoyl and N,N-di-($C_{1-12}$ alkyl) carbamoyl, with the proviso that the substituent $R^{3b}$ is absent if a double bond is present between C9 and C10;
or $R^{3a}$ and $R^{3b}$ together represent oxygen; and
$R^4$ is selected from hydrogen, $C_{1-12}$ alkyl, $C_{1-30}$ alkanoyl, optionally substituted $C_{7-11}$ aroyl and optionally substituted $C_{8-16}$ aralkanoyl;
or a pharmaceutically acceptable salt thereof.

18. A compound of formula (I):

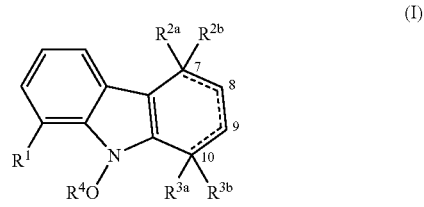

(I)

wherein:
the dotted line represents an optional double bond, with the proviso that at least one single bond is present between C7 and C10;
$R^1$ is selected from $C_{1-12}$ alkyl, which may be optionally substituted by a group selected from hydroxyl, $C_{1-12}$ alkoxy, $C_{1-30}$ alkanoyloxy, optionally substituted $C_{7-11}$, aroyloxy, optionally substituted $C_{8-16}$ aralkanoyloxy, halogen, optionally substituted $C_{6-10}$ aryl, amino, mono-($C_{1-12}$alkyl)amino and di-($C_{1-12}$ alkyl)amino; optionally substituted $C_{6-10}$ aryl; carboxy; $C_{1-30}$ alkoxycarbonyl; optionally substituted $C_{7-11}$ aryloxycarbonyl; optionally substituted $C_{8-16}$ aralkyloxycarbonyl; carbamoyl; N—($C_{1-12}$ alkyl)carbamoyl and N,N-di-($C_{1-12}$ alkyl)carbamoyl;
$R^{2a}$ and $R^{2b}$ are independently selected from hydrogen, hydroxy, $C_{1-12}$ alkyl, $C_{1-30}$ alkanoyl, optionally substituted $C_{7-11}$ aroyl, optionally substituted $C_{8-16}$ aralkanoyl, $C_{1-12}$ alkoxy, $C_{1-30}$ alkanoyloxy, optionally substituted $C_{7-11}$ aroyloxy and optionally substituted $C_{8-16}$ aralkanoyloxy, with the proviso that the substituent $R^{2b}$ is absent if a double bond is present between C7 and C8;

or $R^{2a}$ and $R^{2b}$ together represent oxygen;

$R^{3a}$ and $R^{3b}$ are independently selected from hydrogen; halogen; hydroxy; amino; mono-($C_{1-12}$ alkyl)amino; di-($C_{1-12}$ alkyl)amino; $C_{1-12}$ alkoxy; $C_{1-30}$ alkanoyloxy; optionally substituted $C_{7-11}$ aroyloxy; optionally substituted $C_{8-16}$ aralkanoyloxy; $C_{1-12}$ alkyl, which may be optionally substituted by a group selected from hydroxy, $C_{1-12}$ alkoxy, $C_{1-30}$ alkanoyloxy, optionally substituted $C_{7-11}$ aroyloxy, optionally substituted $C_{8-16}$ aralkanoyloxy, halogen, optionally substituted $C_{6-10}$ aryl, amino, mono-($C_{1-12}$ alkyl)amino and di-($C_{1-12}$ alkyl)amino; optionally substituted $C_{6-10}$ aryl; $C_{1-30}$ alkanoyl, optionally substituted $C_{7-11}$ aroyl; optionally substituted $C_{8-16}$ aralkanoyl; carboxy; $C_{1-30}$ alkoxycarbonyl; optionally substituted $C_{7-11}$ aryloxycarbonyl; optionally substituted $C_{8-16}$ aralkyloxycarbonyl; carbamoyl; N—($C_{1-12}$ alkyl) carbamoyl and N,N-di-($C_{1-12}$ alkyl) carbamoyl, with the proviso that the substituent $R^{3b}$ is absent if a double bond is present between C9 and C10;

or $R^{3a}$ and $R^{3b}$ together represent oxygen; and $R^4$ is selected from hydrogen, $C_{1-12}$ alkyl, $C_{1-30}$ alkanoyl, optionally substituted $C_{7-11}$ aroyl and optionally substituted $C_{8-16}$ aralkanoyl;

or a pharmaceutically acceptable salt thereof.

19. A compound according to claim 18, wherein $R^{2a}$ and $R^{2b}$ are independently selected from hydrogen, hydroxy, $C_{1-6}$ alkoxy and $C_{1-12}$ alkanoyloxy, or $R^{2a}$ and $R^{2b}$ together represent oxygen.

20. A compound according to claim 18, wherein $R^{2a}$ and $R^{2b}$ are independently selected from hydrogen, hydroxy and $C_{1-4}$ alkoxy, or $R^{2a}$ and $R^{2b}$ together represent oxygen.

21. A compound according to claim 18, wherein $R^{2a}$ and $R^{2b}$ together represent oxygen.

22. A compound according to claim 18, wherein $R^{3a}$ and $R^{3b}$ are independently selected from hydrogen; hydroxy; $C_{1-6}$ alkoxy; $C_{1-12}$ alkanoyloxy; $C_{1-6}$ alkyl, which may be optionally substituted by a group selected from hydroxy, $C_{1-6}$ alkoxy and $C_{1-12}$ alkanoyloxy; $C_{1-12}$ alkanoyl; carboxy and $C_{1-12}$ alkoxycarbonyl; or $R^{3a}$ and $R^{3b}$ together represent oxygen.

23. A compound according to claim 18, wherein $R^{3a}$ and $R^{3b}$ are independently selected from hydrogen; hydroxy; $C_{1-4}$ alkyl, which is substituted by a group selected from hydroxy and $C_{1-4}$ alkoxy; $C_{1-6}$ alkanoyl; carboxy and $C_{1-6}$ alkoxycarbonyl.

24. A compound according to claim 18, wherein $R^{2a}$ and $R^{2b}$ independently selected from hydroxy, hydroxymethyl, $C_{1-4}$ alkanol and carboxy.

25. A compound according to claim 18, wherein one of $R^{2a}$ and $R^{3b}$ is hydroxy and the other is formyl.

26. A compound according to claim 18, wherein a double bond is present between C8 and C9.

27. A compound according to claim 18, wherein double bonds are present between C7 and C8 and between C9 and C10.

28. A pharmaceutical preparation which contains as active ingredient a compound according to claim 18, or a pharmaceutically acceptable salt thereof.

* * * * *